(12) United States Patent
Chesnin

(10) Patent No.: US 8,562,557 B2
(45) Date of Patent: Oct. 22, 2013

(54) SMALL DIAMETER DUAL LUMEN CATHETER

(75) Inventor: Kenneth J. Chesnin, Philadelphia, PA (US)

(73) Assignee: Medical Components, Inc., Harleysville, PA (US)

( * ) Notice: Subject to any disclaimer, the term of this patent is extended or adjusted under 35 U.S.C. 154(b) by 578 days.

(21) Appl. No.: 12/121,426

(22) Filed: May 20, 2008

(65) Prior Publication Data

US 2008/0294091 A1    Nov. 27, 2008

Related U.S. Application Data

(60) Provisional application No. 60/931,916, filed on May 25, 2007.

(51) Int. Cl.
    *A61M 3/00*    (2006.01)
(52) U.S. Cl.
    USPC .......................................................... 604/43
(58) Field of Classification Search
    USPC ................ 604/523–524, 526, 528, 95.03–4, 604/96.01, 164.01, 43, 48, 93.01, 284
    See application file for complete search history.

(56) References Cited

U.S. PATENT DOCUMENTS

| | | | |
|---|---|---|---|
| 4,601,697 A | | 7/1986 | Mammolenti et al. |
| 4,619,643 A | * | 10/1986 | Bai ................. 604/43 |
| 5,167,623 A | | 12/1992 | Cianci et al. |
| 5,219,335 A | | 6/1993 | Willard et al. |
| 5,364,344 A | | 11/1994 | Beattie et al. |
| 5,478,326 A | | 12/1995 | Shiu |
| 5,531,719 A | | 7/1996 | Takahashi |
| 5,676,659 A | | 10/1997 | McGurk |
| 5,800,409 A | | 9/1998 | Bruce |
| 5,810,789 A | * | 9/1998 | Powers et al. ............. 604/523 |
| 5,851,203 A | | 12/1998 | vanMuiden |
| 5,895,378 A | | 4/1999 | Nita |
| 6,030,369 A | | 2/2000 | Engelson et al. |
| 6,280,423 B1 | | 8/2001 | Davey et al. |
| 6,453,185 B1 | | 9/2002 | O'Keefe |
| 6,979,313 B1 | | 12/2005 | Meek et al. |
| 7,229,429 B2 | * | 6/2007 | Martin et al. .............. 604/43 |
| 2006/0206094 A1 | | 9/2006 | Chesnin et al. |

OTHER PUBLICATIONS

Medcomp Drawing No. 1977-860, "4F Single Reverse Taper Polyurethane PICC", dated Jul. 22, 2002 (1 sheet, redacted).
Medcomp Drawing No. 1978-860, "4F Double Reverse Taper Polyurethane PICC", dated Jul. 22, 2002 (1 sheet, redacted).
Bard Access Systems Brochure, "Poly Per-Q-Cath PICC", dated 2003 (2 pages).
Various photographs, product, "Poly Per-Q-Cath PICC, 4F Single", Bard Access Systems, Inc., Salt Lake City, UT (4 photographs).
Various photographs, product, "Poly Per-Q-Cath PICC, 4F Double", Bard Access Systems, Inc., Salt Lake City, UT (4 photographs).

* cited by examiner

*Primary Examiner* — Kevin C. Simons
*Assistant Examiner* — Deanna K Hall
(74) *Attorney, Agent, or Firm* — Glenn M. Massina, Esq.; Fox Rothschild LLP

(57) ABSTRACT

A multiple lumen catheter (110,150) having at least first and second lumens (112,114; 152,154). At least one of the first and second lumens (112,152) is generally C-shaped in cross-section, with a septum wall (120,160) dividing the first and second lumens providing a generally straight side to the C-shaped cross-section. A stylet or guide wire (130) may be disposed along the C-shaped cross-section lumen (112,152, 154) having a larger diameter than one used with catheters of the same outer diameter but that have lumens of only D-shaped or circular shaped cross-sections.

4 Claims, 1 Drawing Sheet

SMALL DIAMETER DUAL LUMEN CATHETER

CROSS-REFERENCE TO RELATED APPLICATIONS

This application claims priority from U.S. Provisional Patent Application Ser. No. 60/931,916 filed May 25, 2007.

FIELD OF THE INVENTION

This invention relates to the field of medical devices, and more particularly to implantable catheters such as for infusion and hemodialysis.

BACKGROUND OF THE INVENTION

Catheter assemblies, and particularly catheter assemblies for use in hemodialysis, are known that have one, two or more lumens extending from a distal end to a proximal end, where the distal end is placed in a blood vessel of a patient, such as the jugular vein, with the proximal end extending from the patient for each lumen to be connected to a respective conduit of a hemodialysis machine. Customarily, each lumen of the catheter assembly is first connected to a respective extension tube within a hub body, and the extension tube is terminated in a luer connector to facilitate connection with and disconnection from the conduit of the hemodialysis machine and commonly the extension tube has disposed therealong a clamp, such as a Roberts clamp, for temporarily closing the conduit when necessary. Implanted catheter assemblies are connected to medical apparatus such as hemodialysis apparatus through the luer connectors, and then disconnected therefrom, all through many cycles; such connection and disconnection involves the catheter assembly undergoing many cycles of stress and strain especially focused at the proximal end where the catheter proximal end enters the hub which connects the catheter lumens to respective extension tubes, or where a single lumen catheter enters its luer connector directly instead of via a hub and extension tube.

It is desired to provide an assurance against occluding or kinking of the catheter lumens, as well as greater strength, at the connection of the catheter and the hub, or at the connection of a single lumen catheter luer connection where no hub is utilized.

Certain catheter assemblies, termed PICC catheters (for peripherally inserted central catheters), are implanted through a vessel entry on an arm of the patient, known as axillary placement. But, usually, the catheter assembly is secured to the torso of the patient in a manner to prevent any dislocation of the distal tips of the catheter lumens from any movement along the vessel after initial placement at the catheterization site. This manner of securement is usually accomplished by a process termed tunneling, in which the proximal portion of the catheter assembly outside of the vessel is tunneled subcutaneously near the vessel entry site, typically beneath the clavicle of the patient, whereafter the hub is sutured or otherwise secured to the patient. By this process, during the connection with and disconnection from the hemodialysis machine of the extension tubes, there is no stress or strain passed to the distal end of the catheter assembly that might tend to dislodge the distal lumen tips from the desired location along the vessel.

The orientation of the tunneled portion of the catheter assembly is not axially aligned with the distal portion of the catheter assembly and in fact a relatively sharp bend may be made in the catheter assembly distally of the tunneled portion during placement.

Catheters are conventionally produced in various sizes depending on desired uses, and their outer diameters are measured in units termed "french" or "F", with one F equaling 0.013 inches or 0.32 millimeters. The largest sized catheters utilized for vascular placement may have an outer diameter of about 17 F, and range to smaller sizes. Diameters of 5 F are the smallest sized dual-lumen catheters that are presently preferred in that they present little difficulty with insertion therethrough of small wires or stylets, or that have sufficient strength and thus less kink susceptibility. Even smaller sized catheters are known, however (4 F or less), such as are used with small adolescents and adults. When the catheter outer diameter is almost the same size as the inner diameter of the vessel within which it is implanted, certain problems are associated with catheters after they are vascularly in a patient; for example, development of phlebitis and thrombosis is known in such situations.

It is desired to provide a catheter with a very small outer diameter, especially a dual lumen catheter, thereby minimizing the tendency of phlebitis or thrombosis or the like, to develop. Such a small diameter catheter is disclosed in U.S. Patent Publication No. US 2006/0206094 A1, which provides a catheter assembly wherein the catheter outer diameter is enlarged for at least some of its length proximate the proximal end adjacent the hub, relative to the remainder of the catheter extending to the distal end. The inner diameter of the lumen or lumens remains constant; in a dual-lumen catheter, the inner septum wall between the lumens may also increase in thickness. A very small diameter dual lumen catheter (2.6 F) disclosed in the application provides two circular lumens each with a very small diameter of about 0.011 in (0.028 mm), sufficiently large for an 0.009 inch guide wire (0.23 mm) or 18 GA, and which is less likely to induce phlebitis, thrombosis or the like after implantation. This very small diameter catheter also benefits from an enlarged proximal end diameter, for resistance to occlusion and kinking. The use of stylets with catheters provides rigidity to the catheter during insertion of the catheter into the patient. The catheter could also be inserted over a guide wire, where the guide wire too would provide rigidity and guidance into and through the vasculature.

It is desired to provide a small diameter catheter suitable for use with stylets or guide wires that provide a sufficiently great level of rigidity to the small diameter catheter during patient placement.

BRIEF SUMMARY OF THE INVENTION

The present invention is a small diameter multiple lumen catheter, wherein at least one of the lumens is adapted to receive therethrough a stylet or guide wire. In one embodiment, for a dual lumen catheter, the cross-sectional shape of at least one lumen is generally C-shaped, with the septum defining a straight side to the C-shape. The C-shaped cross-section maximizes lumen height enabling use of relatively larger diameter stylets or guide wires. If the other lumen remains D-shaped, then the septum is offset from the axis in the direction toward the D-shaped lumen. In another embodiment, the cross-sectional shapes of both lumens are generally C-shaped, thus providing greater outer wall thickness at both sides of the septum that separates the lumens from each other.

The modified lumen cross-sectional shapes of the present invention provide for lumens of small double lumen catheters having a maximized height that allow for use of a relatively large stylet or guide wire with such catheters than known small diameter catheters, that is, a stylet or guide wire that is up to 30% larger than is able to be used with prior art lumens of small diameter dual lumen catheters. Use of one of the fluid flow lumens for insertion of a stylet or guide wire, of course, eliminates the need for the catheter to have a separate lumen for the stylet or guide wire, thus enabling the catheter to have a minimized outer diameter. Further, the lumen design provides more lumen stability than comparable designs, to help prevent catheter kinking. Also, the lumen design provides increased tensile strength by increasing the material cross-sectional area (by about 25%) when compared to the prior art double-D cross-sectional configuration.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
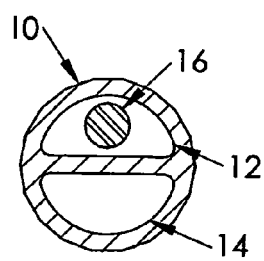
FIG. 1 is a cross-sectional view of a PRIOR ART small diameter catheter, wherein the lumen cross-sectional shape is D-shaped, with a guide wire seen disposed along one lumen.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

In FIG. 1, the prior art dual lumen catheter 10 is shown to have two lumens 12,14 each of which has a D-shaped cross-sectional shape, and shown in one lumen 12 is a guide wire 16. Exemplary dimensions for the catheter 10 are: a French size of 2.6 F (about 0.035 in or 0.89 mm); the height of lumen 12 or 14 is about 0.011 in (0.028 mm); and the minimum thickness of the septum is 0.004 in (0.10 mm). The diameter of guide wire 16 capable of fitting within and along lumen 12 is 0.009 in (0.23 mm), or 18 GA. In this arrangement, because of vasculature bends, the guide wire easily is urged into the confined corners of the D-shaped lumen thus greatly increasing the frictional resistance to moving the catheter relatively along the guide wire and increasing the difficulty for the practitioner.

Figure 2:
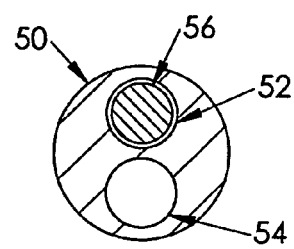
FIG. 2 is a cross-sectional view of a PRIOR ART small diameter catheter, wherein the lumen cross-sectional shape is circular, again with a guide wire seen disposed along one lumen.

In FIG. 2, the prior art dual lumen catheter 50 is shown to have two lumens 52,54 each of which has a circular cross-sectional shape, and shown in one lumen 52 is a guide wire 56. Exemplary dimensions for the catheter 50 are a French size of 2.6 F (the same as that of the prior art catheter of FIG. 1; the height of lumen 52 or 54 (i.e., the critical dimension) is about 0.012 in (0.30 mm); and the septum thickness is about 0.003 in (0.08 mm). The diameter of guide wire 56 capable of fitting within and along lumen 12 is 0.009 in (0.23 mm), or 18 GA.

Figure 3:
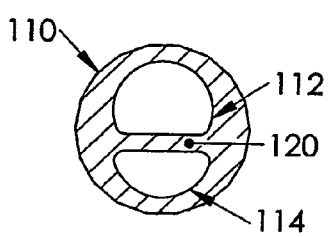
FIG. 3 is a cross-sectional view of a first embodiment of catheter of the present invention.
Figure 4:
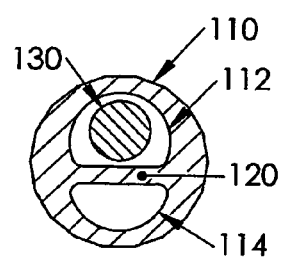
FIG. 4 is a cross-sectional view of the catheter of FIG. 3 wherein a stylet is emplaced in the C-shaped lumen.

The present invention is shown in a first embodiment of dual lumen catheter 110 in FIGS. 3 and 4. Catheter 110 has a diameter of 2.6 French, the same as the diameters of the prior art catheters of FIGS. 1 and 2 for enabling meaningful comparison. A first lumen 112 is shown to have a generally C-shaped cross-sectional shape, while the second lumen 114 is D-shaped in cross-section. It is seen in FIGS. 3 and 4 that first lumen 112 includes one straight side wall, defined by one side of septum 120, while the remaining side walls are arcuate, circumscribing an arc of greater than 180°, the first lumen thus being C-shaped in cross-section. Septum 120 is seen to be offset from the center of the cross-section toward the second lumen 114. The dimensions of first lumen 112 has a width taken parallel to the septum, of 0.020 in (0.51 mm) and a height taken orthogonally to the septum (the critical dimension), of 0.015 in (0.38 mm). In FIG. 4, a stylet 130 is disposed in first lumen 112. The stylet 130 may have a diameter of up to 0.013 in (0.33 mm) and thus is larger than the stylet or guide wire possible to be used in the prior art catheters of FIGS. 1 and 2 even though the outer diameter of the catheter is the same.

Figure 5:
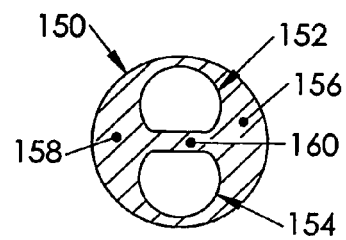
FIG. 5 is a cross-sectional view of a second embodiment of catheter of the present invention.

In FIG. 5, dual lumen catheter 150 has a diameter of 3 French and includes two lumens 152, 154 each of which is generally C-shaped. The first and second lumens each have cross-sectional configurations that are the same as first lumen 112 of FIGS. 3 and 4, with a septum 160 separating lumens 152,154 from each other. Each of lumens 152,154 are of sufficient size to accept therethrough a stylet or guide wire of up to 0.014 in (0.36 mm) in diameter. Side walls 156,158 at ends of septum 160 are seen to be thickened compared to the thickness of the outer walls at other locations about the catheter's circumference, thus enhancing the strength of the catheter and enhancing the resistance to catheter kinking, and the lumens have no confined corners for frictionally gripping the relatively smaller stylet or guide wire as in the prior art catheter lumen D-shaped cross-sections.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A multiple lumen catheter for use in fluid transmission to and from a patient's vasculature, comprising:
    a catheter having a cross-section that is circular with a diameter of less than 5 French,
    the catheter having at least first and second lumens separated by a septum, wherein the septum defines a continuous straight side to the first lumen while the remaining sides thereof are arcuate defining a substantially constant-radius arc of greater than 180°,
    whereby the first lumen's height orthogonal to the septum is maximized enabling receipt therethrough of a comparably larger stylet or guide wire, and the catheter walls at laterally opposite ends of the septum are enlarged in cross-sectional area relative to catheter walls at locations orthogonal to the septum, thereby minimizing catheter kinking orthogonal to the orientation of the septum.

2. The multiple lumen catheter as set forth in claim 1, wherein the catheter is a dual lumen catheter.

3. The multiple lumen catheter as set forth in claim 2, wherein the septum also defines a continuous straight side to the second lumen cross-section with the remaining sides thereof being arcuate defining a substantially constant-radius arc of greater than 180°, whereby the lumen height of each lumen is maximized and the catheter walls at laterally opposite ends of the septum are enlarged in cross-sectional area relative to catheter walls at locations orthogonal to the septum, thereby minimizing catheter kinking orthogonal to the orientation of the septum.

4. The multiple lumen catheter as set forth in claim 3, wherein the septum defines a continuous straight side to the second lumen.

* * * * *